United States Patent
Müller et al.

(10) Patent No.: US 7,429,465 B2
(45) Date of Patent: Sep. 30, 2008

(54) PROCESS FOR ANALYZING TEAR FLUID

(75) Inventors: Achim Müller, Grossostheim (DE); Roland Schmieder, Aschaffenburg (DE); Katharina Schmid, Rodgau (DE)

(73) Assignee: Novartis AG, Basel (CH)

( * ) Notice: Subject to any disclaimer, the term of this patent is extended or adjusted under 35 U.S.C. 154(b) by 425 days.

(21) Appl. No.: 10/653,866

(22) Filed: Sep. 3, 2003

(65) Prior Publication Data

US 2005/0176158 A1 Aug. 11, 2005

(30) Foreign Application Priority Data

Sep. 13, 2002 (EP) .................. 02020618

(51) Int. Cl.
G01N 33/00 (2006.01)
A61B 5/00 (2006.01)

(52) U.S. Cl. ..................... 435/40.5; 600/573

(58) Field of Classification Search ............. 435/4, 435/40.5; 604/294, 372, 297, 573; 600/573
See application file for complete search history.

(56) References Cited

U.S. PATENT DOCUMENTS

| 4,526,178 A | 7/1985 | Opel | ................... 128/760 |
| 2004/0181172 A1* | 9/2004 | Carney et al. | ............... 600/573 |
| 2007/0043283 A1* | 2/2007 | Cohan et al. | ................. 600/345 |

FOREIGN PATENT DOCUMENTS

| DE | 32 18 999 | 12/1983 |
| EP | 0 641 806 | 1/1998 |
| EP | 0 932 635 | 7/2001 |

OTHER PUBLICATIONS

Meakin et al. "Thermal analysis of poly(2-hydroxyethyl methacrylate)(pHEMA) hydrogels" J. Materials Sci: Material Med. (2003) 14: 9-15.*
Wedler, C. "Analysis of biomaterials deposited on soft contact lenses" J. Biomed. Mater. Res. (1977) 11: 525-535.*

* cited by examiner

*Primary Examiner*—Sandra E Saucier
*Assistant Examiner*—Susan Hanley
(74) *Attorney, Agent, or Firm*—Jian Zhou

(57) ABSTRACT

The present invention concerns a process for analyzing an analyte in a hydrogel contact lens following its wear on the eye, comprising the steps of
(a) physically or chemically inducing a volume reduction of the hydrogel contact lens and thereby squeezing the analyte out of the polymer material making up the contact lens and
(b) feeding the analyte obtained according to step (a) into an analyzer.

The process of the invention provides a new concept for noninvasively measuring various analytes occurring in the tear fluid that is comfortable to the user.

12 Claims, No Drawings

PROCESS FOR ANALYZING TEAR FLUID

This application claims benefit under 35 USC § 119 of European patent application No. EP 02020618.1 filed Sep. 13, 2002, the contents of which are incorporated herein by reference.

The present invention concerns a process for analyzing components of the tear fluid and devices useful for this purpose. In particular, the invention is based on the use of specific hydrogel contact lenses, which subsequently to the incorporation of tear fluid components in the hydrogel matrix during wear on the eye may be shrinked thereby dispensing said components and making them available for external analysis.

It is known from DE-3,218,999 C1 to use a hydrogel contact lens in combination with an analytical unit for examining the tear fluid. A hydrated hydrogel contact lens is thus put on the eye for a time sufficient to exchange the saline storage solution with the tear fluid. The lens is then removed from the eye and is transferred to an analytical unit for detecting tear fluid components. However, the components to be analyzed and the procedure of analysis are not further specified. In particular, the document does not address at all the question of how to remove a captured tear fluid component from the hydrogel matrix in order to allow a quantitative measurement. In fact, it turns out that simple equilibration with a test fluid is by far insufficient to leach a component out of the hydrogel contact lens to a sufficient extent. The problem to be solved within the present invention is thus to find a mode of how to use a hydrogel contact lens for collecting tear fluid components and then to ensure that said components may be leached out—without compromising the sensitivity by dilution—completely afterwards and thus may be provided for quantitative and qualitative measurements.

It now has surprisingly been found a process that allows tear fluid components being incorporated in the hydrogel matrix of a contact lens during wear to be squeezed out of the contact lens by physically or chemically reducing the volume of the contact lens.

The present invention therefore in one aspect concerns a process for analyzing an analyte in a hydrogel contact lens following its wear on the eye, comprising the steps of
(a) physically or chemically inducing a volume reduction of the hydrogel contact lens and thereby squeezing the analyte out of the polymer material making up the contact lens, and
(b) feeding the analyte obtained according to step (a) into an analyzer.

Presence and/or concentration of a wide variety of analytes can be measured using the process of the invention. In principle all components come into consideration that are part of the tear fluid. Such analytes include, but are not limited to, electrolytes and small molecules (e.g., sodium, potassium, chloride, phenylalanine, uric acid, galactose, glucose, cysteine, homocysteine, calcium, ethanol, acetylcholine and acetylcholine analogs, ornithine, blood urea nitrogen, creatinine), metallic elements (e.g., iron, copper, magnesium), polypeptide hormones (e.g., thyroid stimulating hormone, growth hormone, insulin, luteinizing hormones, chorionogonadotrophic hormone), chronically administered medications (e.g., dilantin, phenobarbital, propranolol), acutely administered medications (e.g., cocaine, heroin, ketamine), small molecule hormones (e.g., thyroid hormones, ACTH, estrogen, estradiol, progesterone, testosterone, cortisol, and other metabolic steroids), markers of inflammation and/or allergy (e.g., histamine, IgE, cytokines), lipids (e.g., cholesterol), plasma proteins and enzymes (e.g., complement, coagulation factors, liver function enzymes, heart damage enzymes, ferritin), markers of infection (e.g., virus components, immunoglobulins such as IgM, IgG, etc., proteases, protease inhibitors), and/or metabolites (e.g., lactate, ketone bodies).

The process of the invention can be used to monitor the course of therapy or the level of disease in mammals, including primates and, preferably, humans. In addition, because the process of the invention provides a way to detect analytes noninvasively, it provides distinct advantages over more traditional forms of monitoring such levels. The process of the invention also is useful for diagnostic purposes, for example to test for pregnancy, to assess blood chemistry (electrolytes, $Ca_2PO_4$, magnesium, bilirubin, alkaline phosphatase, lactate dehydrogenase, alanine aminotransferase, etc.), and to detect infection (e.g., by detecting components of viruses such as CMV, EBV, hepatitis, and HIV, or bacteria, such as *Staphlococcus, Streptococcus*, etc.).

Particular preferred analytes, which may be measured according to the process of the invention are products of metabolism such as glucose and hormones.

The hydrogel contact lenses used in the process of the invention are usually worn for a single measurement; during said measurement one or, preferably, more than one analyte may be determined concurrently. Both qualitative and preferably quantitative measurements can be performed.

Hydrogel contact lenses useful in the claimed process are in general contact lenses having a water uptake of at least about 20%. Preferably the water contents of the hydrogel lenses is from about 35 to 99%, more preferably from 50 to 90% and in particular from 60 to 80%.

In addition, the polymer making up the hydrogel contact lens preferably comprises functional groups that allow a chemical reaction including a volume reduction, or are able to bind a further compound that allows a chemical reaction including a volume reduction.

Examples of suitable hydrogel materials are:
(i) Homo- and copolymers of hydroxyethyl methacrylate (HEMA); such as HEMA homopolymers, copolymers of HEMA and a crosslinker such as mono-, di-, tri- or tetra-ethyleneglycol dimethacrylate, or copolymers of HEMA and one or more further hydrophilic monomers, such as N-vinyl pyrrolidone or N,N-dimethyl acrylamide, and optionally being further crosslinked, for example, with one of the above-mentioned crosslinkers.
(ii) Homo- or copolymers derived from a crosslinkable polyalkylene oxide as disclosed, for example in EP-A-0,932,635, EP-A-0,958,315, EP-A-0-961,941 or EP-A-1,017,734.
(iii) Modified polyvinyl alcohols, for example those disclosed in EP-A-0641806; A preferred material is a polyvinyl alcohol which is obtainable by crosslinking a polyvinyl alcohol prepolymer having a molecular weight of at least about 2 000 that, based on the number of hydroxy groups of the polyvinyl alcohol, comprises from approximately 0.5 to approximately 80% of units of formula

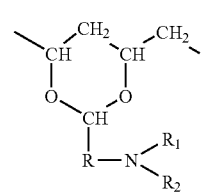

(1)

wherein R is $C_1$-$C_8$-alkylene, $R_1$ is hydrogen or $C_1$-$C_7$-alkyl and $R_2$ is an olefinically unsaturated, electron-attracting, copolymerizable radical preferably having up to 25 carbon atoms.

$R_2$ is, for example, an olefinically unsaturated acyl radical of formula $R_3$—CO—, in which $R_3$ is an olefinically unsaturated copolymerizable radical having from 2 to 24 carbon atoms, preferably from 2 to 8 carbon atoms, especially preferably from 2 to 4 carbon atoms. In another embodiment, the radical $R_2$ is a radical of formula

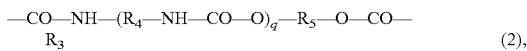
(2), wherein q is zero or one and $R_4$ and $R_5$ are each independently $C_2$-$C_8$-alkylene, $C_6$-$C_{12}$-arylene, a saturated divalent $C_6$-$C_{10}$-cycloaliphatic group, $C_7$-$C_{14}$-arylenealkylene or $C_7$-$C_{14}$-alkylenearylene or $C_{13}$-$C_{16}$-arylenealkylenearylene, and $R_3$ is as defined above.

The prepolymer used for the manufacture of the modified polyvinyl alcohol is therefore especially a derivative of a polyvinyl alcohol having a molecular weight of at least about 2 000 that, based on the number of hydroxy groups of the polyvinyl alcohol, comprises from approximately 0.5 to approximately 80% of units of formula

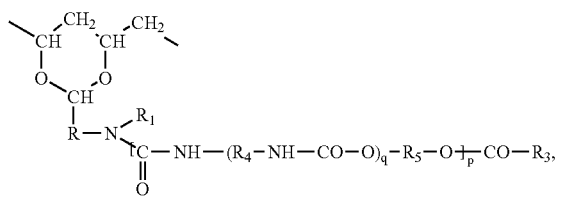
(3)

wherein R is $C_1$-$C_8$-alkylene, $R_1$ is hydrogen or $C_1$-$C_7$-alkyl, p is zero or one, q is zero or one, $R_3$ is an olefinically unsaturated copolymerizable radical having from 2 to 8 carbon atoms and $R_4$ and $R_5$ are each independently $C_2$-$C_8$-alkylene, $C_6$-$C_{12}$-arylene, a saturated divalent $C_6$-$C_{10}$-cycloaliphatic group, $C_7$-$C_{14}$-arylenealkylene or $C_7$-$C_{14}$-alkylenearylene or $C_{13}$-$C_{16}$-arylenealkylenearylene.

An alkylene radical R may be straight-chained or branched. Suitable examples include octylene, hexylene, pentylene, butylene, propylene, ethylene, methylene, 2-propylene, 2-butylene and 3-pentylene. Alkylene R has preferably 1 to 6 and especially preferably 1 to 4 carbon atoms. The meanings methylene and butylene are especially preferred.

$R_1$ is preferably hydrogen or $C_1$-$C_4$-alkyl, especially hydrogen.

Alkylene $R_4$ or $R_5$ preferably has from 2 to 6 carbon atoms and is especially straight-chained. Suitable examples include propylene, butylene, hexylene, dimethylethylene and, especially preferably, ethylene.

Arylene $R_4$ or $R_5$ is preferably phenylene that is unsubstituted or is substituted by $C_1$-$C_4$-alkyl or $C_1$-$C_4$-alkoxy, especially 1,3-phenylene or 1,4-phenylene or methyl-1,4-phenylene.

A saturated divalent cycloaliphatic group $R_4$ or $R_5$ is preferably cyclohexylene or cyclohexylene-$C_1$-$C_4$-alkylene, for example cyclohexylenemethylene, that is unsubstituted or is substituted by one or more methyl groups, such as, for example, trimethylcyclohexylenemethylene, for example the divalent isophorone radical.

The arylene unit of alkylenearylene or arylenealkylene $R_4$ or $R_5$ is preferably phenylene, unsubstituted or substituted by $C_1$-$C_4$-alkyl or $C_1$-$C_4$-alkoxy, and the alkylene unit thereof is preferably $C_1$-$C_8$-alkylene, such as methylene or ethylene, especially methylene. Such radicals $R_4$ or $R_5$ are therefore preferably phenylenemethylene or methylenephenylene.

Arylenealkylenearylene $R_4$ or $R_5$ is preferably phenylene-$C_1$-$C_4$-alkylene-phenylene, for example phenyleneethylenephenylene.

The radicals $R_4$ and $R_5$ are each independently preferably $C_2$-$C_6$-alkylene; phenylene, unsubstituted or substituted by $C_1$-$C_4$-alkyl; cyclohexylene; cyclohexylene-$C_1$-$C_4$-alkylene, unsubstituted or substituted by $C_1$-$C_4$-alkyl; phenylene-$C_1$-$C_4$-alkylene; $C_1$-$C_4$-alkylenephenylene; or phenylene-$C_1$-$C_4$-alkylene-phenylene.

The olefinically unsaturated copolymerizable radical $R_3$ having from 2 to 24 carbon atoms is preferably $C_2$-$C_{24}$-alkenyl, especially $C_2$-$C_8$-alkenyl and especially preferably $C_2$-$C_4$-alkenyl, for example ethenyl, 2-propenyl, 3-propenyl, 2-butenyl, hexenyl, octenyl or dodecenyl. The meanings ethenyl and 2-propenyl are preferred, so that the group —CO—$R_3$ is preferably the acyl radical of acrylic or methacrylic acid.

The divalent group —$R_4$—NH—CO—O— is present when q is one and absent when q is zero. Prepolymers in which q is zero are preferred.

The divalent group —CO—NH—($R_4$—NH—CO—O)$_q$—$R_5$—O— is present when p is one and absent when p is zero. Prepolymers in which p is zero are preferred.

In prepolymers in which p is one the index q is preferably zero. Prepolymers in which p is one, the index q is zero and $R_5$ is $C_2$-$C_8$-alkylene are especially preferred.

A preferred prepolymer used for the manufacture of the modified polyvinyl alcohols is therefore especially a derivative of a polyvinyl alcohol having a molecular weight of at least about 2000 that, based on the number of hydroxy groups of the polyvinyl alcohol, comprises from approximately 0.5 to approximately 80% of units of formula (3) in which R is $C_1$-$C_6$-alkylene, p is zero and $R_3$ is $C_2$-$C_8$-alkenyl.

A further preferred prepolymer used for the manufacture of the modified polyvinyl alcohols is therefore especially a derivative of a polyvinyl alcohol having a molecular weight of at least about 2000 that, based on the number of hydroxy groups of the polyvinyl alcohol, comprises from approximately 0.5 to approximately 80% of units of formula (3), in which R is $C_1$-$C_6$-alkylene, p is one, q is zero, $R_5$ is $C_2$-$C_6$-alkylene and $R_3$ is $C_2$-$C_8$-alkenyl.

A further preferred prepolymer used for the manufacture of the modified polyvinyl alcohols is therefore especially a derivative of a polyvinyl alcohol having a molecular weight of at least about 2000 that, based on the number of hydroxy groups of the polyvinyl alcohol, comprises from approximately 0.5 to approximately 80% of units of formula (3) in which R is $C_1$-$C_6$-alkylene, p is one, q is one, $R_4$ is $C_2$-$C_6$-alkylene, phenylene, unsubstituted or substituted by $C_1$-$C_4$-alkyl, cyclohexylene or cyclohexylene-$C_1$-$C_4$-alkylene, unsubstituted or substituted by $C_1$-$C_4$-alkyl, phenylene-$C_1$-$C_4$-alkylene, $C_1$-$C_4$-alkylene-phenylene or phenylene-$C_1$-$C_4$-alkylene-phenylene, $R_5$ is $C_2$-$C_6$-alkylene and $R_3$ is $C_2$-$C_8$-alkenyl.

The prepolymers used for the manufacture of the modified polyvinyl alcohols are preferably derivatives of polyvinyl alcohol having a molecular weight of at least about 2000 that, based on the number of hydroxy groups of the polyvinyl alcohol, comprises from approximately 0.5 to approximately 80%, especially from 1 to 50%, preferably approximately from 1 to 25%, preferably approximately from 2 to 15% and especially preferably approximately from 3 to 10%, of units of formula (3). Prepolymers according to the invention which are provided for the manufacture of contact lenses comprise, based on the number of hydroxy groups of the polyvinyl alcohol, especially from approximately 0.5 to approximately 25%, especially approximately from 1 to 15% and especially preferably approximately from 2 to 12%, of units of formula (3).

Derivatized polyvinyl alcohols according to the invention preferably have an average molecular weight $M_n$ of at least 10 000. As an upper limit the polyvinyl alcohols may have an average molecular weight of up to 1 000 000. Preferably, the polyvinyl alcohols have a molecular weight of up to 300 000, especially up to approximately 100 000 and especially preferably up to approximately 50 000.

Polyvinyl alcohols suitable in accordance with the invention usually have a poly(2-hydroxy)ethylene structure. The polyvinyl alcohols may, however, also comprise hydroxy groups in the form of 1,2-glycols, such as copolymer units of 1,2-dihydroxyethylene, as may be obtained, for example, by the alkaline hydrolysis of vinyl acetate/vinylene carbonate copolymers.

The polyvinyl alcohol prepolymers may be further modified by one or more compounds imparting additional functionality such as, for example, amino, epoxy, carboxy, or carboxylic acid ester, anhydride or halide functionality. The prepolymers may comprise such additional functional groups in an amount of, for example, up to 20% and preferably up to 10%, each based on the total number of hydroxy groups of the polyvinyl alcohol.

In addition, the polyvinyl alcohols used may also comprise small a proportion, for example up to 50%, preferably up to 25% and more preferably up to 15%, of copolymer units of, for example, ethylene, propylene, acrylamide, methacrylamide, dimethacrylamide, hydroxyethyl methacrylate, methyl methacrylate, methyl acrylate, ethyl acrylate, vinylpyrrolidone, hydroxyethyl acrylate, allyl alcohol, styrene or similar customarily used comonomers.

The modified polyvinyl alcohols that are derived from a prepolymer comprising units of formula (1) or (3) are known, for example, from EP-A-0641806 and may be prepared according to the processes described therein.

Shrinkage of the contact lenses after their wear on the eye may be performed by any physical and/or chemical method or reaction, that is able to compress a polymer network thereby leading to a volume contraction. Examples of physical methods are applying a temperature gradient or adding salts/electrolytes to the polymer in order to provide segregation. Preferably, the shrinkage of the contact lens is induced by a suitable chemical reaction.

According to a preferred embodiment of the invention, the shrinkage of the hydrogel contact lens material is achieved by a further crosslinking step. One possibility is to treat the contact lens with a di- or multifunctional compound having two or more functional groups that are coreactive with functional groups of the polymer. For example, a polymer comprising hydroxy or amino groups may be crosslinked with a di- or polyisocyanate or di- or polycarboxylic acid or a derivative thereof.

Preferably, additional crosslinkable groups, for example C—C double bonds, are chemically introduced into the polymer making up the contact lens, or latent crosslinkable groups present in the polymer making up the contact lens are converted to crosslinkable groups; the thus modified contact lens is then further crosslinked thermally or preferably photochemically, especially by the action of UV light, the further crosslinking step leading to a volume contraction.

The introduction of crosslinkable C—C double bonds to a polymer material comprising functional groups, for example hydroxy, amino or epoxy groups, may be carried out, for example, by reacting the functional groups of the polymer with an unsaturated compound comprising a functional group that is co-reactive to the functional groups of the polymer. Examples of suitable unsaturated compounds are isocyanatoethyl methacrylate (IEM), an unsaturated carboxylic acid derivative, for example acryloyl chloride or acrylic acid anhydride, an unsaturated amine, for example allyl amine, glycidyl methacrylate (GMA), 2-vinyl-4,4-dimethyl-azlactone (VAL) or, particularly in case of a polyvinyl alcohol hydrogel, an unsaturated acetal, for example an acetal of formula

wherein R' and R" are each independently, for example, hydrogen, $C_1$-$C_4$-alkyl or $C_2$-$C_4$-alkanoyl, preferably hydrogen, methyl, ethyl or acetyl, for R the above given meanings and preferences apply, and for $R_1$ and $R_2$ the above given meanings and preferences apply or —$NR_1R_2$ together form a group

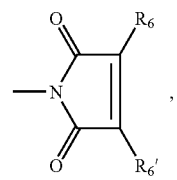

wherein $R_6$ and $R_6'$ are each independently hydrogen or methyl, preferably each methyl. The reactions of IEM, GMA, VAL or a carboxy derivative with primary or secondary hydroxy groups or amino groups of the contact lens polymer material are known per se and may be carried, for example, as described in textbooks of Organic Chemistry. The reaction of acetals such as a compound of formula (4) above with a PVA polymer is likewise known, for example, from EP-A-0641806. In addition, the reaction of epoxy groups of the polymer with an unsaturated amine or a carboxy derivative is known from textbooks of Organic Chemistry.

Preferably, the hydrogel contact lens already contains latent polymerizable groups which may be activated in a simple way following their wear on the eye.

A further embodiment of the invention is therefore directed to a polyvinyl alcohol, which is obtainable by crosslinking a polyvinyl alcohol prepolymer having a molecular weight of at least about 2 000 that, based on the number of hydroxy groups of the polyvinyl alcohol, comprises from about 0.5 to about 80% of units of the formula (1) or (3) given above and from about 0.5 to about 80% of units of formula

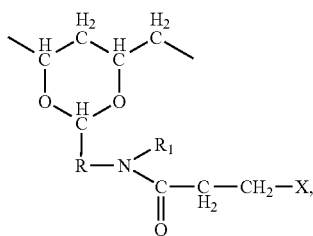

(5)

wherein for R and $R_1$ each the above given meanings and preferences apply, and X is, for example, halogen, in particular bromine or especially chlorine.

A preferred polyvinyl alcohol hydrogel according to the invention is obtainable from an polyvinyl alcohol prepolymer comprising from 1 to 25% and particularly 3 to 10% units of formula (3), wherein p is 0 and $R_3$ is ethenyl —CH=$CH_2$ or 2-propenyl —C($CH_3$)=$CH_2$, and from 3 to 60%, preferably from 5 to 50% and particularly from 10 to 30% units of formula (5). In formulae (3) and (5) above R is each most preferably methylene (—$CH_2$—) and $R_1$ is each preferably hydrogen.

Biomedical moldings, in particular contact lenses, may be prepared from an above mentioned polyvinyl alcohol prepolymer comprising both units of the formula (3) and (5) by photocrosslinking it in a suitable mold, in particular in a contact lens mold, in analogy to the process as described in EP-A-0641806. The units of formula (5) do not react and thus remain unchanged in the resulting contact lens. After being worn on the eye the contact lens may be treated in an alkaline medium thereby converting the groups of formula —$NR_1$—C(O)—$CH_2$—$CH_2$—X to polymerizable groups —$NR_1$—C(O)—CH=$CH_2$. For example, a short treatment with an alkali metal hydroxide solution, such as sodium hydroxide or potassium hydroxide under ambient conditions is sufficient to convert the halogenethyl carbonamido groups to vinyl carbonylamido groups.

Following the addition or activation of further crosslinkable groups the hydrogel contact lenses may be further crosslinked according to methods known per se, for example, by the action of heat or by irradiation. Photocrosslinking using, for example, visible light or UV light, in particular UV light, is preferred. The contact lenses are photocrosslinked, for example, in solution, for example in an aqueous solution, or, preferably, in the absence of a solvent. Photocrosslinking can be carried out according to the invention in a very short time, for example in less than five minutes, preferably in ≦1 minute, especially in 1 to 60 seconds, especially preferably, in 2 to 30 seconds.

In the case of photocrosslinking, it is appropriate to add a photoinitiator, which can initiate radical crosslinking. Examples thereof are familiar to the person skilled in the art and suitable photoinitiators that may be mentioned specifically are benzoin methyl ether, 1-hydroxycyclohexylphenyl ketone, or Darocure® or Irgacure® types, for example Darocure® 1173 or Irgacure® 2959. The amount of photoinitiator may be selected within wide limits, an amount of up to 0.05 g/g of contact lens polymer and especially of up to 0.003 g/g of contact lens polymer having proven beneficial.

A further preferred embodiment relates to a contact lens that is obtainable from a polymerizable or crosslinkable material comprising two types of C—C double bonds, one that reacts under conditions customary for the crosslinking/polymerizing of acrylate type monomers or prepolymers and a second one that does not react under conditions customary for the crosslinking/polymerizing of acrylate type monomers or prepolymers but needs specific conditions, for example a specific initiator, for example a triplet initiator.

An example is a polyvinyl alcohol, which is obtainable by crosslinking a polyvinyl alcohol prepolymer having a molecular weight of at least about 2 000 that, based on the number of hydroxy groups of the polyvinyl alcohol, comprises from about 0.5 to about 80% of units of the formula (1) or (3) given above and from about 0.5 to about 80% of units of formula

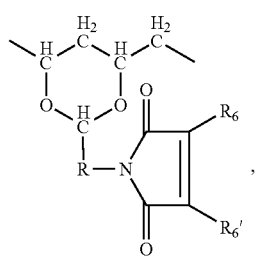

(6)

wherein for R, $R_6$ and $R_6'$ each the above given meanings and preferences apply.

Biomedical moldings, in particular contact lenses, may be prepared from an above mentioned polyvinyl alcohol prepolymer comprising both units of the formula (3) and (6) by photocrosslinking it in a suitable mold, in particular in a contact lens mold, in analogy to the process as described in EP-A-0641806. The units of formula (6) do not react and thus remain unchanged in the resulting contact lens. After being worn on the eye the contact lens may be further crosslinked by subjecting the C—C double bonds of the maleinic imide units to a polymerization reaction using a triplet initiator.

Contact lenses having been crosslinked according to any one of the above mentioned methods show a considerable shrinkage of, for example more than 5% and preferably ≧10%, relative to their original size. In addition, they lose a considerable amount of water including ingredients contained in the water. Said aqueous solution originating, for example, from a contact lens that has been equilibrated with the tear fluid of the lens wearer during wear on the eye may be fed into an analytical chip, apparatus or the like for qualitative or quantitative measurements.

Analytical equipment useful for the detection and measurement of the various ingredients of the tear fluid are known per se and commercially available in part. For example, various devices for the qualitative or quantitative measurement of blood sugar or different kinds of hormones are known for long.

In a preferred embodiment of the invention two or more of the steps of (i) adding crosslinkable groups to/activate crosslinkable groups in the contact lens;

(ii) shrinking the lens, preferably by crosslinking and in particular by photocrosslinking;

(iii) feeding the aqueous solution having been squeezed out of the lens into an analyzer, i.e. an analytical unit, chip or the like; and (iv) analyzing the squeeze qualitatively and/or quantitatively;

are combined in one unit, apparatus or the like.

The present invention provides a new concept for noninvasively measuring various analytes occurring in the tear fluid that is very comfortable to the user. This is, for example, because the user just has to wear a contact lens for a certain time period, for example for a time period from about 30 minutes to 24 hours, and preferably from about 1 to 18 hours, then remove it from the eye and place it in a suitable apparatus for shrinkage and analysis in order to get a desired result. The process is especially well-suited for once-a-day measurements in combination with a contact lens for daily wear.

The following Examples further illustrate the present invention.

Introduction of Crosslinkable Groups into a Contact Lens and Crosslinking of the Modified Material

EXAMPLES 1-3

Three groups of small vials comprising each a contact lens manufactured according to Example 15i of EP-A-0641806 (modified PVA material) are prepared: The first group comprises the lens in dest. water while the second and third group comprise the lens in a 0.5% or 1.0% by weight aqueous solution of N-acrylaminoacealdehyde dimethylacetal, (NAAADA) respectively. A small amount of conc. HCl (about 0.6 ml) is added to each sample, and the vials are then shaken for about 20 hours at ambient temperature. The contact lenses are then removed from the vials and rinsed with water (5 ml, about 30 minutes). The procedure is repeated twice. Following dabbing each contact lens is put in a vial comprising 5 ml of a 0.1% by weight aqueous solution of Irgacure®2959 (photoinitiator), and the vials are stored in a refrigerator for 4 days. 4 contact lenses each of groups 1, 2 and 3 are irradiated for 4 or 8 seconds with a UV lamp (2.44 mW/cm$^2$). The diameter of an untreated contact lens as well as the diameters of the lenses as treated above are then determined (Table 1).

TABLE 1

(average values):

| Example | NAAADA contents [% by weight] | Lens diameter [mm] 4 s irradiation time | Lens diameter [mm] 8 s irradiation time | Lens diameter [mm] untreated |
|---|---|---|---|---|
| Control | — | — | — | 13.93 |
| 1 | 0.0 (just water) | 13.95 | 13.94 | — |
| 2 | 0.5 | 12.55 | 12.11 | — |
| 3 | 1.0 | 11.93 | 11.87 | — |

Following dabbing and after having established a constant weight, the weight of the contact lenses is determined as follows (Table 2).

TABLE 2

(average values)

| Example | NAAADA contents [% by weight] | contact lens weight [mg] | weight loss [mg] | weight loss [%] |
|---|---|---|---|---|
| 1 (4s) | 0.0 | 22.92 | — | — |
| 1 (8s) | 0.0 | 24.04 | — | — |
| 2 (4s) | 0.5 | 17.45 | 5.47 | 24 |
| 2 (8s) | 0.5 | 18.08 | 5.99 | 25 |
| 3 (4s) | 1.0 | 18.08 | 5.54 | 24 |
| 3 (8s) | 1.0 | 16.81 | 7.23 | 30 |

The invention claimed is:

1. A process for analyzing at least one analyte contained in tear fluid which is present in a hydrogel contact lens which has been worn on the eye, wherein the hydrogel is a polymer, comprising the steps of:
   (a) chemically inducing a reduction in the volume of the hydrogel lens by crosslinking the polymer, thereby squeezing tear fluid that contains the at least one analyte from the polymer; and
   (b) contacting the tear fluid that contains the at least one analyte according to step (a) with an analytical instrument to detect the analyte.

2. The process of to claim 1, wherein the analyte is glucose or a hormone.

3. The process of claim 1, wherein more than one analyte is analyzed concurrently.

4. The process of claim 1, wherein the hydrogel contact lens comprises a HEMA homo- or copolymer, a homo or copolymer derived from a crosslinkable polyalkylene oxide or a modified polyvinyl alcohol.

5. The process of claim 1, wherein the hydrogel contact lens comprises a polyvinyl alcohol which is obtained by crosslinking a polyvinyl alcohol prepolymer having a molecular weight of at least about 2000 and comprising, based on the number of hydroxy groups, from approximately 0.5 to approximately 80 % of units of formula

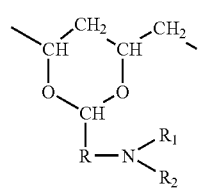

(1)

wherein R is $C_1$-$C_8$-alkylene, $R_1$ is hydrogen or $C_1$-$C_7$-alkyl and $R_2$ is an olefinically unsaturated, electron-attracting, copolymerizable radical having up to 25 carbon atoms.

6. The process of claim 5, wherein R is methylene, $R_1$ is hydrogen, and $R_2$ is a group —CO—$R_3$, wherein $R_3$ is ethenyl or 2-propenyl.

7. The process of claim 5, wherein the polyvinyl alcohol prepolymer additionally comprises units of formula (5)

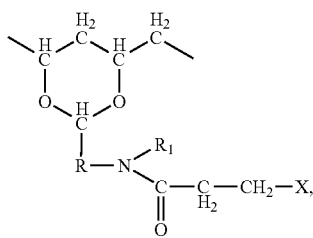
(5)

wherein R is $C_1$-$C_8$-alkylene, $R_1$ is hydrogen or $C_1$-$C_7$-alkyl, and X is halogen.

8. The process of claim 5, wherein the polyvinyl alcohol prepolymer additionally comprises units of formula (6)

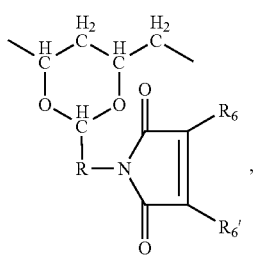
(6)

wherein $R_6$ and $R_6'$ are each independently hydrogen or methyl, and R is as defined.

9. The process of claim 1, wherein the crosslinking step is accomplished by reacting the polymer with an unsaturated compound that is capable of reacting with the polymer to produce a modified hydrogel polymer having unsaturated groups and photocrosslinking the modified polymer to produce a crosslinked hydrogel polymer.

10. The process of claim 7, inducing the volume reduction of the contact lens by reacting the polymer comprising at least one unit of formula (5) with an unsaturated compound that is capable of reacting with the polymer to produce a modified polymer having unsaturated groups that are capable of undergoing a polymerization reaction and photocrosslinking the modified polymer to produce a crosslinked polymer.

11. The process of claim 8, inducing the volume reduction of the contact lens by subjecting the polymer comprising at least one unit of formula (6) to a polymerization reaction with a triplet initiator.

12. The process of claim 1, further comprising the step of reacting the polymer with an unsaturated compound that is capable of reacting with the hydrogel polymer to produce a modified polymer having unsaturated groups that are capable of undergoing a polymerization reaction.

* * * * *